(12) United States Patent
Lin et al.

(10) Patent No.: US 6,803,129 B2
(45) Date of Patent: Oct. 12, 2004

(54) ORGANIC LIGHT EMITTING DIODE AND ORGANIC LUMINESCENT MATERIALS THEREOF

(75) Inventors: Hsien-Chang Lin, Jubei (TW); Chih-Hao Kung, Kaohsiung (TW); Chung-Cheng Pai, Taipei (TW); Shwu-Ju Shieh, Taipei (TW); Tzu-Chin Tang, Hsinchu (TW)

(73) Assignee: RiTdisplay Corporation, Hsinchu (TW)

( * ) Notice: Subject to any disclaimer, the term of this patent is extended or adjusted under 35 U.S.C. 154(b) by 0 days.

(21) Appl. No.: 10/423,738

(22) Filed: Apr. 25, 2003

(65) Prior Publication Data

US 2004/0086746 A1 May 6, 2004

(30) Foreign Application Priority Data

Oct. 25, 2002 (TW) .......................... 91125123 A (51) Int. Cl.$^7$ .................... H05B 33/14; C09K 11/06
(52) U.S. Cl. ................ 428/690; 428/917; 313/504; 313/506; 252/301.16; 546/183; 546/26; 549/23; 549/28; 549/381; 549/399; 549/400; 549/404; 549/406
(58) Field of Search .................. 428/690, 917; 313/504, 506; 252/301.16; 546/26, 183; 549/23, 28, 381, 399, 400, 404, 406

(56) References Cited

FOREIGN PATENT DOCUMENTS

EP          0797376 A2 *   3/1997

* cited by examiner

*Primary Examiner*—Dawn Garrett
(74) *Attorney, Agent, or Firm*—J. C. Patents

(57) ABSTRACT

The present invention relates to an organic light emitting diode (OLED) device, comprising an anode disposed on a substrate, an organic EL layer disposed on the anode and a cathode disposed on the organic EL layer. The material of the organic EL layer comprises a compound modified from coumarin compounds, as denoted in a following formula (1):

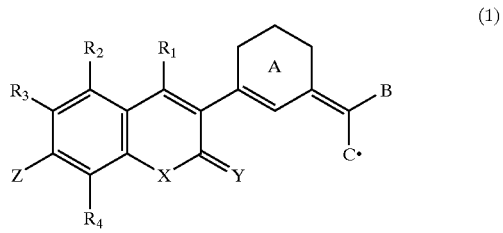

(1)

21 Claims, 2 Drawing Sheets

ORGANIC LIGHT EMITTING DIODE AND ORGANIC LUMINESCENT MATERIALS THEREOF

CROSS-REFERENCE TO RELATED APPLICATION

This application claims the priority benefit of Taiwan application serial no. 91125123, filed Oct. 25, 2002.

BACKGROUND OF THE INVENTION

1. Field of Invention

The present invention relates to an organic light emitting diode (OLED). More particularly, the present invention relates to a red light organic light emitting diode device and organic luminescent materials thereof

2. Description of Related Art

So far, lightweight displays with high efficiency, such as, liquid crystal displays, have been widely developed. However, quite a few problems still exist in liquid crystal displays, including narrow viewing angles, response time not short enough for high-speed animations and the need of back light modules resulting in more power consumption. In addition, it is difficult to manufacture large-scale panels for the liquid crystal displays.

Therefore, a new flat display technology is recently developed to solve the above problems, which is the organic light emitting diode (OLED) display. The organic light emitting diode is a display component, taking advantage of self-luminescent characteristics of its organic luminescent or fluorescent materials for display. The OLED mainly comprise a pair of electrodes and an organic electroluminescence (EL) layer. The organic EL layer includes luminescent materials. The holes and electrons from the transparent anode and the metal cathode can cause the luminescent materials to form exitons, thus resulting in light emission (electroluminescence).

As disclosed in Applied Physics Letters, Vol. 51, No. 12, pp. 913–15 (1987), C. W. Tang and S. A. VanSlyke reported a double layered organic light emitting diode, consisting of an organic EL layer and a hole transport layer or a electron transport layer, together with an electrode pair. As holes are injected from anode and electrons are injected from cathode, passing through the hole transportlayer or the electron transport layer, to the organic EL layer, the holes and electrons combine in the organic EL layer so as to generate electroluminescence. The luminescent material of the organic EL layer can generate luminescence with different chromaticity, depending on the energy differences (gaps) between the ground state and the excited state of the materials.

In the Japanese Journal of Applied Physics, Vol. 27, No. 2, pp. L269–L271 (1988) and Journal of Applied Physics, Vol. 65, No. 9, pp. 3610–16 (1989), a three-layered structure of the organic light emitting diode is reported. In addition to the electrode pair, the structure consists of an organic EL layer, a hole transport layer and a electron transport layer. From these reports, it is proved that development toward low driving voltage and high brightness is possible.

For full-color displays, it is essential to have colors of high purity. Because of using organic materials as luminescent materials, the color of the light (luminescence), the wavelengths of the red, green and blue light, can be modified by changing the design of the molecular structures.

However, there are some problems existing in the organic light emitting diodes, especially in developing red light luminescent materials with high stability and high efficiency. At present, for the red light luminescent materials, 4-(dicyanomethylene-6-(p-dimethylaminostyryl)-2-methyl-4H-pyran) (DCM) or its derivatives doped in tris(8-quinolinol)aluminum (AlQ3) are commonly used. However, these materials can not meet the requirements of brightness and purity for the full-color organic light emitting diode devices.

SUMMARY OF THE INVENTION

Accordingly, the present invention provides an organic light emitting diode (OLED) device and materials of its organic electroluminescence (EL) layer thereof, which fulfills the requirement for the full-color OLED display.

Accordingly, the present invention provides an OLED device and luminescent materials of the organic EL layer thereof, in order to offer an OLED device with high efficiency and red light luminescent materials with high color purity.

The present invention provides an OLED device and materials of the organic EL layer thereof. The OLED device comprises a first electrode disposed on a substrate, an organic EL layer disposed on the first electrode and a second electrode disposed on the organic EL layer. The luminescent material of the organic EL layer disclosed in the present invention is a compound modified from coumarin compounds, denoted as the following formula (1):

(1)

wherein $R_1$~$R_4$ individually represents hydrogen, substituted or non-substituted alkyl group, substituted or non-substituted cycloalkyl group, substituted or non-substituted alkoxyl group, substituted or non-substituted alkenyl group, substituted or non-substituted amino group, substituted or non-substituted aryl group, heterocyclic group, aryloxy group, and substituted or non-substituted propenyloxy group. In addition, $R_3$~$R_4$ can be the fused ring formed from any two of the aforementioned groups. Z represents —$OR_5$ or —$NR_6R_7$. X and Y individually represents oxygen atom, sulfur atom or —$NR_8$. A is substituted or non-substituted polyterphenyl (including cyclohexenyl group as shown in the following formula (2) and naphthalenylidenyl group as shown in formula (3)). B and C are electron-pulling groups, either the same groups or different groups, such as, cyano group, indandione, benzoimidazole, benzooxazole or benzothiazole.

Specifically, $R_1$~$R_4$ individually represents hydrogen, substituted or non-substituted alkyl group with 1–10 carbon atoms, substituted or non-substituted cycloalkyl group with 1–10 carbon atoms, substituted or non-substituted alkoxyl group with 1–10 carbon atoms, substituted or non-substituted alkenyl group with 1–10 carbon atoms, substituted or non-substituted amino group, substituted or non-substituted aryl group with 6–30 carbon atoms, heterocyclic group with 6–30 carbon atoms, aryloxy group with 6–30 carbon atoms, and substituted or non-substituted propenyloxy group with 1–10 carbon atoms. $R_5$~$R_8$ individually represents hydrogen, substituted or non-substituted alkyl group with 1–10 carbon atoms, substituted or non-substituted cycloalkyl group with 1–10 carbon atoms, substituted or non-substituted alkenyl group with 1–10 carbon atoms, substituted or non-substituted aryl group with 6–30 carbon atoms, heterocyclic group with 6–30 carbon atoms, aryloxy group with 6–30 carbon atoms. $R_{14}$~$R_{19}$ individually represents hydrogen or alkyl group.

(2)

(3)

B and C are independently electron-withdrawing groups, such as, dicyano group, cyano group, indandione, benzoimidazole, benzooxazole or benzothiazole, as shown in the following formulas (4)–(9).

(4)

(5)

(6)

(7)

(8)

(9)

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
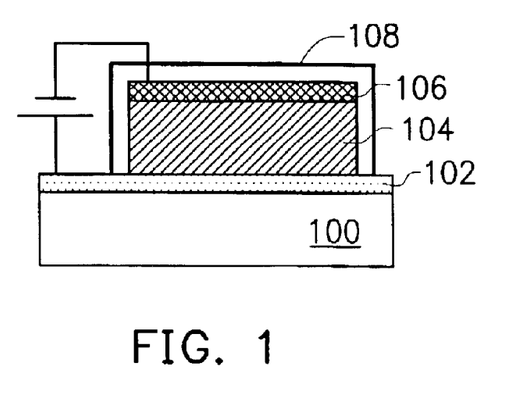
FIG. 1 is a schematic cross-sectional view of an OLED device according to the first preferred embodiment of the present invention.

FIG. 1 is a schematic cross-sectional view of an OLED device according to one preferred embodiment of the present invention.

As shown in FIG. 1, the organic light emitting diode (OLED) is a single-layered structure OLED, comprising a transparent substrate 100, an anode 102, an organic electroluminescence (EL) layer 104, a cathode 106 and a protective layer 108. The transparent substrate 100 is, for example, a glass substrate, a plastic substrate or a flexible substrate. The anode 102 is disposed on the transparent substrate 100. For efficiently injecting holes into the organic EL layer 104, the anode 102 preferably has work function larger than 4.5 eV. The anode 102 is made of indium tin oxide (ITO), tin oxide, gold, silver, platinum or copper, for example.

The organic EL layer 104 is disposed on the anode 102. In addition to the luminescent characteristics, the organic EL layer 104 also has functions of transporting holes and electrons. The material of the organic EL layer 104 is one important feature of the present invention. Preparations and the detailed chemical structures of the materials for the organic EL layer are described hereinafter.

The cathode 106 is disposed on the organic EL layer 104. For efficiently injecting electrons into the organic EL layer 104, the cathode 106 by preference has smaller work function. The cathode 106 is made of indium, aluminum, magnesium-indium alloy, magnesium-aluminum alloy, aluminum-lithium alloy or magnesium-silver alloy, for example.

The protective layer 108 completely covers the OLED device, thus acting as a sealing film for keeping airtight. Direct current is usually applied to the OLED device, however, it is possible to apply pulse current or alternating current to the OLED device. The luminescence of the OLED device is either transmitted from the anode 102 or reflected from the cathode 106.

Figure 2:
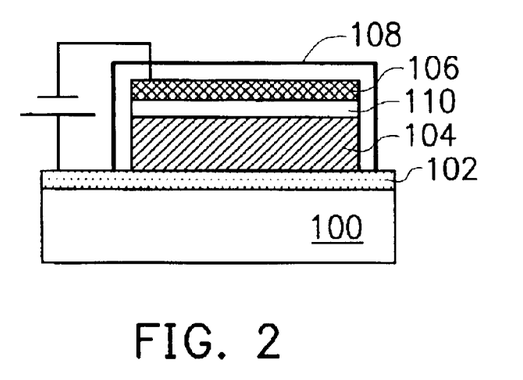
FIG. 2 is a schematic cross-sectional view of an OLED device according to the second preferred embodiment of the present invention.
Figure 3:
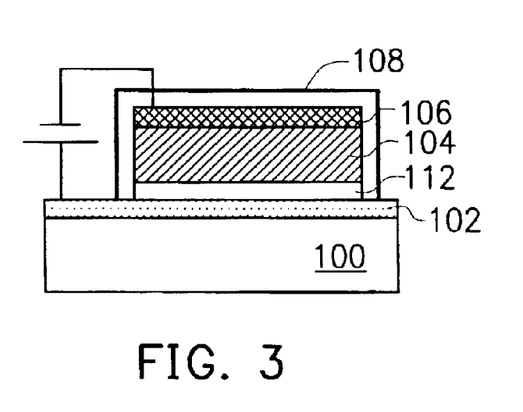
FIG. 3 is a schematic cross-sectional view of an OLED device according to the third preferred embodiment of the present invention.

The OLED device of the present invention can be a double-layered structure OLED, as shown in FIGS. 2 and 3. In FIG. 2, the double-layered structure of the OLED device further comprises an electron transport layer 110 between the organic EL layer 104 and the cathode 106. In FIG. 3, the double-layered structure of the OLED device further comprises a hole transport layer 112 between the organic EL layer 104 and the anode 102.

Figure 4:
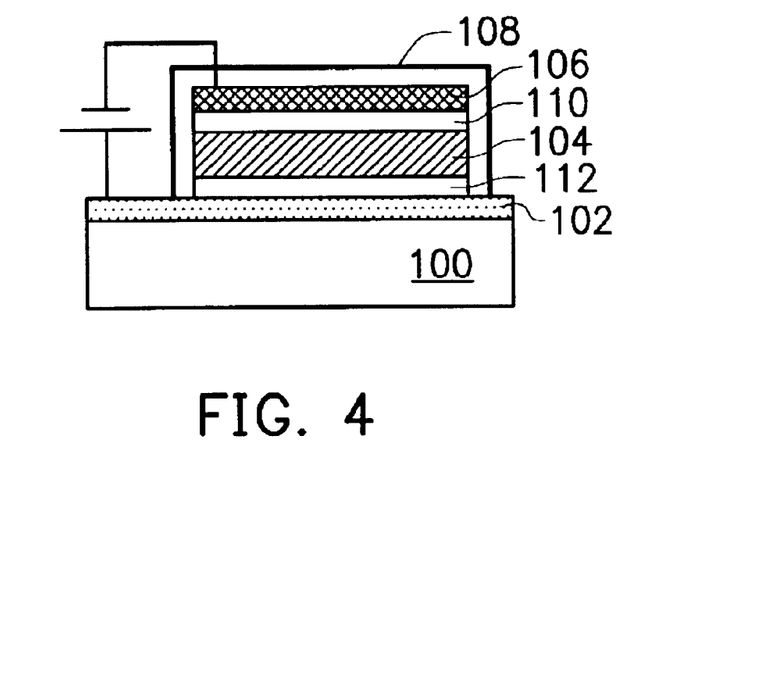
FIG. 4 is a schematic cross-sectional view of an OLED device according to the fourth preferred embodiment of the present invention.

Moreover, the OLED device of the present invention can be a three-layered structure OLED, as shown in FIG. 4. In FIG. 4, the three-layered structure of the OLED device further comprises a hole transport layer 112 between the organic EL layer 104 and the anode 102, along with an electron transport layer 110 disposed between the organic EL layer 104 and the cathode 106.

Figure 5:
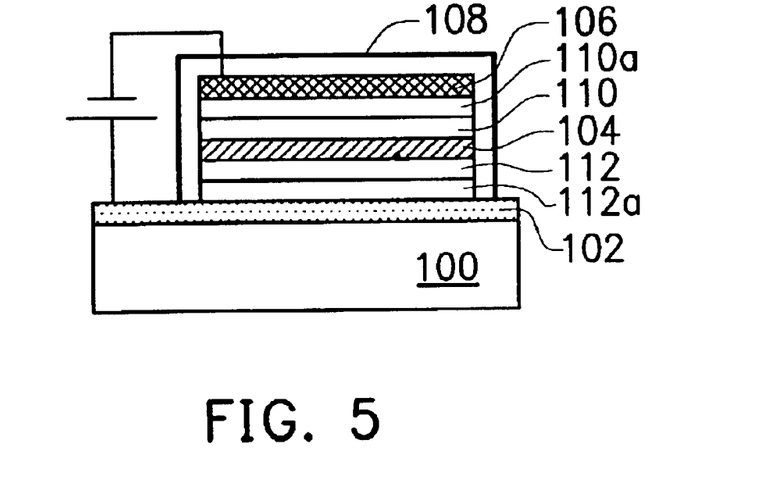
FIG. 5 is a schematic cross-sectional view of an OLED device according to the fifth preferred embodiment of the present invention.

The OLED device of the present invention can be a five-layered structure OLED, as shown in FIG. 5. In FIG. 5, in addition to the electron transport layer 110 between the organic EL layer 104 and the cathode 106, the five-layered structure of the OLED device further comprises an electron injecting layer 110a between the electron transport layer 110 and the cathode 106. Furthermore, together with the hole transport layer 112 between the organic EL layer 104 and the anode 102, the aforementioned five-layered structure of the OLED device further comprises a hole injecting layer 112a between the anode 102 and the hole transport layer 112.

For these OLED devices described above, one of the major features of the present invention is the material selected for forming the organic EL layer 104. The luminescent material of the organic EL layer 104 disclosed in the present invention is a red light luminescent material, described hereinafter.

The luminescent material of the organic EL layer 104 disclosed in the present invention is a compound modified from coumarin compounds, denoted as the following formula (1):

(1)

wherein $R_1$~$R_4$ individually represents hydrogen, substituted or non-substituted alkyl substituted or non-substituted cycloalkyl, substituted or non-substituted alkyloxy, substituted or non-substituted alkenyl, substituted or non-substituted amino group, substituted or non-substituted aryl, substituted or non-substituted heteroaralkyl, substituted or non-substituted aralkyl, and substituted or non-substituted propenyloxy. In addition, $R_3$~$R_4$ can be the fused ring formed from any two of the aforementioned groups. Z represents —$OR_5$ or —$NR_6R_7$. X and Y individually represents oxygen atom, sulfur atom or —$NR_8$. A is substituted or non-substituted polyterphenyl (including cyclohexenyl group as shown in the following formula (2) and naphthalenylidenyl group as shown in formula (3)). B, C are electron-pulling groups, either the same or different groups, such as, cyano group, indandione, benzoimidazole, benzooxazole or benzothiazole.

In detail, $R_1$~$R_{18}$ individually represents hydrogen, substituted or non-substituted alkyl group with 1–10 carbon atoms, substituted or non-substituted cycloalkyl group with 1–10 carbon atoms, substituted or non-substituted alkoxyl group with 1–10 carbon atoms, substituted or non-substituted alkenyl group with 1–10 carbon atoms, substituted or non-substituted amino group, substituted or non-substituted aryl group with 6–30 carbon atoms, heterocyclic group with 6–30 carbon atoms, aryloxy group with 6–30 carbon atoms, and substituted or non-substituted propenyloxy group with 1–10 carbon atoms. $R_5$~$R_8$ individually represents hydrogen, substituted or non-substituted alkyl group with 1–10 carbon atoms, substituted or non-substituted cycloalkyl group with 1–10 carbon atoms, substituted or non-substituted alkenyl group with 1–10 carbon atoms, substituted or non-substituted aryl group with 6–30 carbon atoms, heterocyclic group with 6–30 carbon atoms, aryloxy group with 6–30 carbon atoms. $R_{14}$~$R_{19}$ individually represents hydrogen or alkyl group.

(2)

-continued

(3)

B and C independently are electron-withdrawing groups, such as, dicyano group, cyano group, indandione, benzoimidazole, benzooxazole or benzothiazole, as shown in the following formulas (4)–(9).

(4)

(5)

(6)

(7)

(8)

(9)

In the following paragraphs, several compounds (formulas (10)–(28)) that can be used as materials for forming the organic EL layer of the OLED device in the present invention are listed as follows. The listed compounds are only portions of compounds denoted by formula (1), while the scope of the present invention is not limited thereto.

(10)

(11)

(12)

(13)

(14)

(15)

(16)

(17)

(18)

(19)

(20)

(21)

(22)

(23)

(24)

(25)

(26)

(27)

(28)

It is noted that the coumarin compounds in the above formula (1) can be combined with specific compounds, including specific aromatic mono, di or triamine compounds with aryl or heterocyclic groups, in order to obtain the OLED device with superior functions.

In addition, the coumarin compounds in the above formula (1) can be mixed with specific metal complex compounds (such as, AlQ3), so as to obtain the red light OLED device with premium characteristics.

As for the OLED device of the present invention, the process for forming the organic EL layer with compounds in formula (1) can employ all the possible technology know in the art, including vacuum evaporation, molecular beam evaporation (MBE), soaking in solvent solution, spin coating, casting, bar coding or roll coating. The thickness of the organic EL layer for the OLED device of the present invention can be adjusted based on product requirements. In general, if the thickness of the organic EL layer is too small, defects like pin holes may occur. On the other hand, higher voltage is required if the thickness of the organic EL layer is too large, thus lowering the efficiency. Therefore, the thickness of the organic EL layer for the OLED device of the present invention is preferably in a range of 1 nm to 1 micron, most preferably in a range of 300–5000 Angstroms.

Moreover, all the possible materials commonly used in the field can be used as the material of the hole transport layer for the OLED device in the present invention. The commonly used materials for the hole transport layer include TPD or α-naphylhenyldiamine (NPB), as shown in the following formulas.

TPD

-continued

NPB

As for the electron transport layer for the OLED device in the present invention, all the possible materials commonly used in the field can be used as the material of the electron transport layer. The commonly used materials for the electron transport layer include AlQ3, Bebq2, TAZ or PBD, as listed in the following formulas.

AlQ3

Bebq2

TAZ

PBD

As for the OLED device of the present invention, the process for forming the electron transport layer, the hole transport layer, the electron injecting layer or the hole injecting layer can employ all the possible technology known in the art. For example, the commonly used technology can be vacuum evaporation or spin coating. The thickness of the electron transport layer, the hole transport layer, the electron injecting layer or the hole injecting layer in the OLED device of the present invention can be adjusted based on product requirements. In general, if the thickness of the layer is too small, defects like pin holes may occur. On the other hand, higher voltage is required if the thickness of the layer is too large, thus lowering the efficiency. Therefore, for the OLED device of the present invention, the thickness of the electron transport layer, the hole transport layer, the electron injecting layer or the bole injecting layer is preferably in a range of 1 nm to 1 micron.

In the following paragraphs, one embodiment is used to describe synthesis of a material for an organic EL layer, while the other two embodiments exemplify the OLED device of the present invention. However, these embodiments are merely exemplary, but are not used to limit the scope of the present invention.

Embodiment: Synthesis

In this embodiment, one compound as fisted in formula (14) is used as an example for describing its synthesis.

17.94 g (80 mmole) of Triethylphosphonacetate is added into 20 ml anhydrous THF solvent, followed by adding the mixture solution, under nitrogen atmosphere, into THF solution containing 3.2 g NaH and stirred for 3 hrs. The resultant solution is mixed with THF solution containing 5.61 g (40 mmole) of 3-ethoxy-2-cyclohexen-1-one, and then heated and refluxed under the nitrogen gas for 48 hrs. As the temperature of mixture becomes lower, dichloromethane and water are used for extraction. The organic phase is dried over magnesium sulfate and spin-dried to obtain 4.78 g of formula (14-1) compound, with a production rate of 57%.

(14-1)

2.5 ml Acetic acid and 25 ml 1,4-Dioxane are mixed with 4.78 g of formula (14-1) compound, and then heated and refluxed under the nitrogen gas for 24 hrs. As the temperature of the mixture becomes lower, the mixture solution is spin-dried and the remained liquid is extracted by diethyl ether and water. The organic phase is dried over magnesium sulfate and spin-dried to obtain a brown viscous compound. After purified by chromatography (with ethyl acetate and n-hexane), 1.3 g of a formula (14-2) compound is obtained, with a production rate of 32%.

(14-2)

In the presence of piperidine (0.1 eq), 1.3 g of formula (14-2) compound (1.05 eq) and 1.95 g formula (14-3) compound (1 eq) are mixed with 15 ml acetonitrile, heated and refluxed for 20 hrs. As the temperature of mixture lowers to the room temperature, dichloromethane and water are used for extraction. The organic phase is dried over magnesium sulfate and spin-dried to obtain a black viscous compound. After purified by chromatography (with ethyl acetate and n-hexane), 2.1 g of formula (14-4) compound is obtained, with a production rate of 75%.

(14-3)

(14-4)

In the presence of piperidine (O.1 eq), formula (14-4) compound (1 eq) and malonitrile (1.05 eq) are placed in acetonitrile, heated and refluxed for 4 hrs. As the temperature of mixture lowers to the room temperature, dichloromethane and water are used for extraction. The organic phase is dried over magnesium sulfate and spin-dried to obtain a black viscous compound. After purified by chromatography (with ethyl acetate and n-hexane), 1.9 g of formula (14) compound is obtained, with a production rate of 82%.

(14)

EXAMPLE 1

A three-layered structure OLED device is disclosed herein, as shown in FIG. 4. A glass substrate 100 (100 mm*100 mm in size) is provided and an indium tin oxide (ITO) layer having a thickness of 10 nm is electroplated onto the glass substrate 100. After performing the photolithography and etching steps to the ITO layer, a plurality of pattern regions (10 mm*10 mm in size) are formed, acting as an anode 102. Under the vacuum of $10^{-5}$ Pa, a vacuum evaporation step is performed to electroplate a hole transport layer 112 having a thickness of about 60 nm on the surface of the anode 102. The hole transport layer 112 is made of NPB, with an evaporation rate of 0.2 nm/sec, for example.

The compound of formula (1) and AlQ3, placed in two different dishes, are evaporated on the hole transport layer 112 at the same time, but with evaporation rates of 0.2 nm/sec and 0.003 nm/sec respectively, so as to form an organic EL layer 104. The organic EL layer 104 preferably has a thickness of about 25 nm.

An electron transport layer 110, for example, a layer of AlQ3 with a thickness of about 25 nm, is formed on the organic EL layer 104 by evaporation with an evaporation rate of 0.2 nm/sec, for example.

A cathode 106 is formed (electroplated) on the electron transport layer 110. The cathode 106 includes a layer of LiF having a thickness of about 1.2 nm and a layer of aluminum having a thickness of about 150 nm, for example. Along with the protective layer, the three-layered structure of the OLED device is completed.

For measuring the luminescent characteristics of the OLED device according to the above embodiment, the device is driven by direct current sources and measured by the Keithly 2000 System. From the measurement, it shows that the luminescence of the device is red light having a wavelength of 600 nm, with threshold voltage of 3V and maximum brightness of 13220 cd/m$^2$.

By using the luminescent materials disclosed in the present invention as materials of the organic EL layer, the resultant red light OLED device has not only high reliability and high efficiency but also high brightness and high color purity. Therefore, it is suitable to apply the red light luminescent materials disclosed in the present invention to the full-color OLED displays.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An organic light emitting diode (OLED) device, comprising:
   a transparent base plate;
   an anode disposed on the transparent base plate;
   an organic electroluminescence (EL) layer disposed on the anode; and
   a cathode disposed on the organic EL layer, wherein the organic EL layer comprises a coumarin compound as denoted in a following formula (1):

(1)

wherein $R_1$~$R_4$ individually represents hydrogen, substituted or non-substituted alkyl, substituted or non-substituted cycloalkyl, substituted or non-substituted alkyloxy, substituted or non-substituted alkenyl, substituted or non-substituted amino group, substituted or non-substituted aryl, substituted or non-substituted heteroaralkyl, substituted or non-substituted aralkyl, and substituted or non-substituted propenyloxy; Z represents —OR$_5$ or —NR$_6$R$_7$; X and Y individually represents oxygen atom, sulfur atom or —NR$_8$; $R_5$~$R_8$ individually represents hydrogen, substituted or non-substituted alkyl, cycloalkyl alkenyl, aryl, heteroaralkyl, aralkyl; A is substituted cyclohexenyl group, non-substituted cyclohexenyl group, substituted naphthalenylidenyl group or non-substituted naphthalenylidenyl group; B and C are electron-pulling groups.

2. The device of claim 1, wherein B and C are either the same functional groups or different functional groups.

3. The device of claim 1, wherein B and C are selected from the group consisting of dicyano, benzoimidazole, benzooxazole and benzothiazole.

4. The device of claim 1, wherein the organic EL layer further comprises a compound selected from the following group consisting of an aromatic amine compound having an aryl group or a heteroaralkyl group, an aromatic diamine compound having an aryl group or a heteroaralkyl group and an aromatic triamine compound having an aryl group or a heteroaralkyl group, in addition to the coumarin compound.

5. The device of claim 1, wherein the organic EL layer further comprises a metal complex compound, in addition to the coumarin compound.

6. The device of claim 5, wherein the metal complex compound includes AlQ3.

7. The device of claim 1, wherein the organic EL layer has a thickness in a range of about 1 nanometer to about 1 micron.

8. The device of claim 1, further comprising an electron transport layer disposed between the anode and the organic EL layer.

9. The device of claim 8, further comprising an electron injecting layer disposed between the electron transport layer and the organic EL layer.

10. The device of claim 1, further comprising a hole transport layer disposed between the cathode and the organic EL layer.

11. The device of claim 10, further comprising a hole injecting layer disposed between the cathode and the hole transport layer.

12. A luminescent material, applied in an organic light emitting diode (OLED) device, the luminescent material comprising a coumarin compound as denoted in a following formula (1):

(1)

, wherein $R_1$~$R_4$ individually represents hydrogen, substituted or non-substituted alkyl, substituted or non-substituted cycloalkyl, substituted or non-substituted alkyloxy, substituted or non-substituted alkenyl, substituted or non-substituted amino group, substituted or non-substituted aryl, substituted or non-substituted heteroaralkyl, substituted or non-substituted aralkyl, and substituted or non-substituted propenyloxy; Z represents —$OR_5$ or —$NR_6R_7$; X and Y individually represents oxygen atom, sulfur atom or —$NR_8$; $R_5$~$R_8$ individually represents hydrogen, substituted or non-substituted alkyl, cycloalkyl, alkenyl, aryl, heteroaralkyl, aralkyl; A is substituted cyclohexenyl group, non-substituted cyclohexenyl group, substituted naphthalenylidenyl group or non-substituted naphthalenylidenyl group; B and C are electron-pulling groups.

13. The material of claim 12, wherein B and C are either the same functional groups or different functional groups.

14. The material of claim 12, wherein B and C are selected from the group consisting of dycno, cyano, benzoimidazole, benzooxazole and benzothiazole.

15. The material of claim 12, further comprising a compound selected from the following group consisting of an aromatic amine compound having an aryl group or a heteroaralkyl group, an aromatic diamine compound having an aryl group or a heteroaralkyl group and an aromatic triamine compound having an aryl group or a heteroaralkyl group, in addition to the coumarin compound.

16. The material of claim 12, further comprising a metal complex compound, in addition to the coumarin compound.

17. The material of claim 16, wherein the metal complex compound includes AlQ3.

18. The device of claim 1, wherein B and C fuse together to be indandione.

19. The device of claim 1, wherein $R_3$ and $R_4$ are joined together to form a fused ring.

20. The material of claim 12, wherein B and C fuse together to be indandione.

21. The material of claim 12, wherein $R_3$ and $R_4$ are joined together to form a fused ring.

* * * * *